US00PP28410P3

(12) United States Plant Patent
Tan

(10) Patent No.: US PP28,410 P3
(45) Date of Patent: Sep. 19, 2017

(54) ***HIBISCUS* PLANT NAMED 'TAHI56'**

(50) Latin Name: *Hibiscus×moscheutos*
Varietal Denomination: TAHI56

(71) Applicant: Alain Tan, Montauban (FR)

(72) Inventor: Alain Tan, Montauban (FR)

( * ) Notice: Subject to any disclaimer, the term of this patent is extended or adjusted under 35 U.S.C. 154(b) by 22 days.

(21) Appl. No.: 14/757,368

(22) Filed: Dec. 22, 2015

(65) Prior Publication Data

US 2017/0094859 P1 Mar. 30, 2017

(30) Foreign Application Priority Data

Sep. 29, 2015 (EM) ..... PBR 2015/2256

(51) Int. Cl.
*A01H 5/02* (2006.01)

(52) U.S. Cl.
USPC ..... Plt./257

(58) Field of Classification Search
USPC ..... Plt./257
See application file for complete search history.

*Primary Examiner* — Susan McCormick Ewoldt
(74) *Attorney, Agent, or Firm* — Penny J. Aguirre

(57) ABSTRACT

A new cultivar of *Hibiscus* plant named 'TAHI56' that is characterized by its upright and well-branched plant habit, its flowers that are very pale purple-white in color with a red eye, its large flowers that grow up to 25 cm in diameter, and its foliage that is green and suffused with greyed purple to brown.

2 Drawing Sheets

Botanical classification: *Hibiscus×moscheutos*.
Cultivar designation: 'TAHI56'.

CROSS REFERENCE TO RELATED APPLICATIONS

This application is co-pending with U.S. Plant Patent Applications filed for 2 plants derived from the same breeding program that are entitled *Hibiscus* Plant Named 'TAHI12' (U.S. Plant patent application Ser. No. 14/757,369) and *Hibiscus* Plant Named 'TAHI16' (U.S. Plant patent application Ser. No. 14/757,377).

BACKGROUND OF THE INVENTION

The present invention relates to a new and distinct cultivar of *Hibiscus* plant botanically known as *Hibiscus×moscheutos* 'TAHI56' and will be referred to hereafter by its cultivar name, 'TAHI56'. 'TAHI56' is a new cultivar of hardy *hibiscus* grown for use as a container and landscape plant.

The new cultivar was developed through an on-going breeding program conducted by the Inventor in Montauban, France. The new cultivar arose from a cross made in September of 2012 between *Hibiscus* 'Summer Storm' (U.S. Plant Pat. No. 20,443) as the female parent and *Hibiscus×moscheutos* 'Griotte' (not patented) as the male parent. 'TAHI56' was selected as a single unique plant in September of 2012 from the resulting seedlings of the above cross.

Asexual propagation of the new cultivar was first accomplished by softwood stem cuttings in Montauban, France in 2012 by the Inventor. Asexual propagation by softwood stem cuttings and tissue culture has determined that the characteristics of the new cultivar are stable and are reproduced true to type in successive generations.

SUMMARY OF THE INVENTION

The following traits have been repeatedly observed and represent the characteristics of 'TAHI56'. These attributes in combination distinguish 'TAHI56' as a new and distinct cultivar of *Hibiscus*.

1. 'TAHI56' exhibits an upright and well-branched plant habit.
2. 'TAHI56' exhibits flowers that are very pale purple-white in color with a red eye.
3. 'TAHI56' exhibits large flowers that grow up to 25 cm in diameter.
4. 'TAHI56' exhibits foliage that is green and suffused with greyed purple to brown.

The female parent plant, 'Summer Storm', is similar to 'TAHI56' in having foliage that is dark in color. 'Summer Storm' differs from 'TAHI56' in having flowers that are pink in color. The male parent plant, 'Griotte', is similar to 'TAHI56' in having foliage that is dark in color. 'Griotte' differs from 'TAHI56' in having flowers that are cherry red in color and foliage that is less dark in color. 'TAHI16' can be compared to cultivars that derived from the same breeding program; 'TAHI12' and 'TAHI16'. 'TAHI12' differs from 'TAHI56' in having pink flowers with more visible veins. 'TAHI16' differs from 'TAHI156' in having flowers that are deep red-pink in color.

BRIEF DESCRIPTION OF THE DRAWINGS

The accompanying colored photographs illustrates the overall appearance and distinct characteristics of the new *Hibiscus*. The photographs were taken of a twelve month-old plant of 'TAHI56' as grown in a 23-cm container in an un-heated greenhouse in Boskoop, The Netherlands.

The photograph in FIG. 1 provides a side view of 'TAHI56' in bloom.

Figure 1:
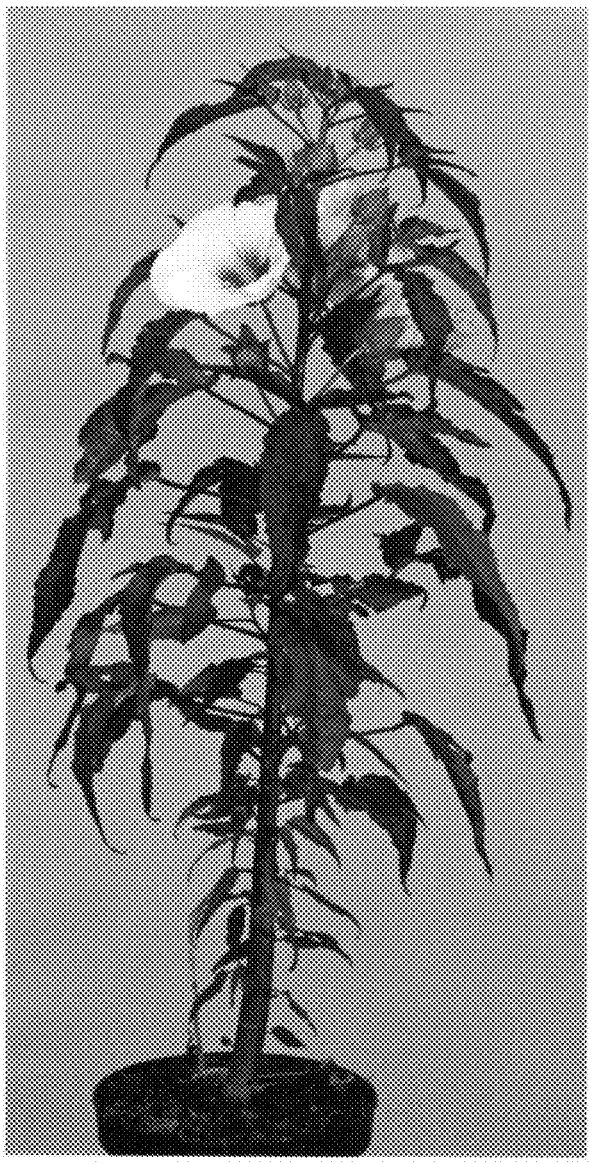
Figure 2:
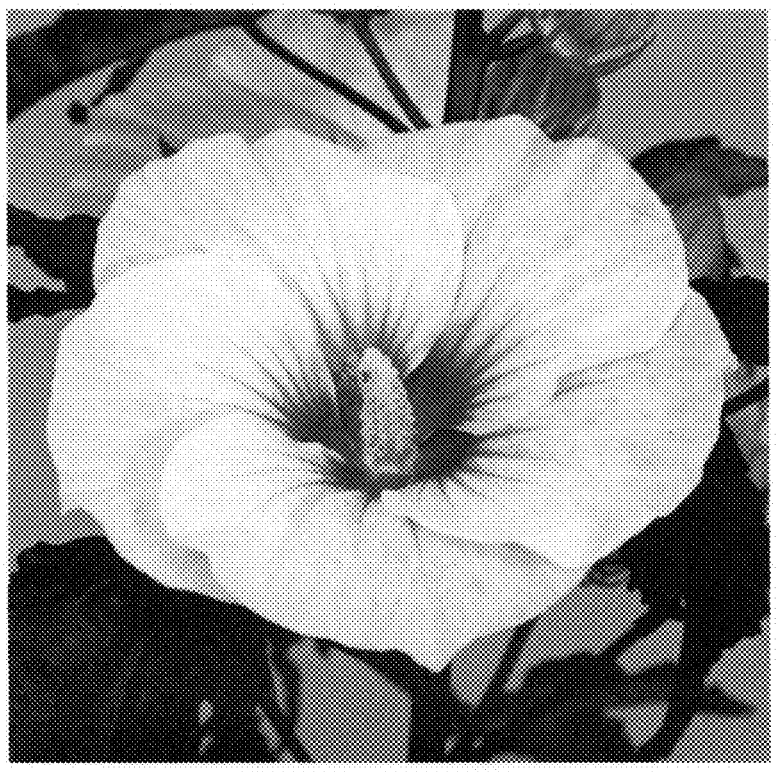

The photograph in FIG. 2 provides a close-up view of a flower of 'TAHI56'.

Figure 3:
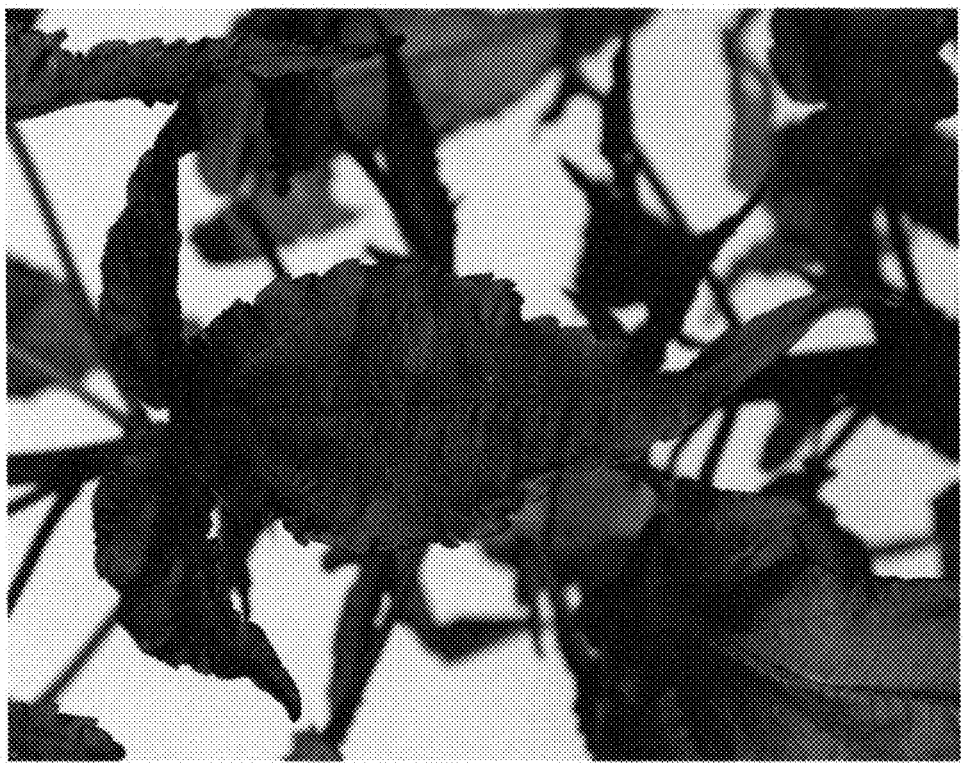

The photograph in FIG. 3 provides a close-up view of a leaf of 'TAHI56'.

The colors in the photographs are as close as possible with the digital photography and printing techniques utilized and the color codes in the detailed botanical description accurately describe the new *Hibiscus*.

DETAILED BOTANICAL DESCRIPTION OF THE PLANT

The following is a detailed description of 12 month-old plants of the new cultivar as grown outdoors in 23-cm container in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

*Blooming period*.—Late summer to beginning of Autumn in The Netherlands.

*Plant type*.—Herbaceous perennial.

*Plant habit*.—Upright, well-branched.

*Height and spread*.—Reaches about 81.7 cm in height and 37.7 cm in spread.

*Cold hardiness*.—At least in U.S.D.A. Zone 5.

*Diseases and pests*.—No susceptibility or resistance to diseases or pests has been observed.

*Root description*.—Fibrous.

*Root development*.—Roots initiate in about 2 weeks and fully develop in about 3 months in a 4-liter container.

*Propagation*.—Softwood stem cuttings and tissue culture.

*Growth rate*.—Moderately vigorous.

Stem description:

*Shape*.—Round.

*Stem color*.—178A.

*Stem size*.—An average of 79.4 cm in length and 1.2 cm in diameter.

*Stem surface*.—Glabrous.

*Stem aspect*.—Upright, in an average angle of 80° to soil level (0°=vertical).

*Stem strength*.—Moderately strong.

*Branching*.—Moderately free branching, an average of 4 lateral branches.

*Internode*.—Average of 1.8 cm.

Foliage description:

*Leaf shape*.—Hastate to narrow ovate.

*Leaf division*.—Simple.

*Leaf base*.—Hastate to truncate.

*Leaf apex*.—Long acuminate.

*Leaf venation*.—Pinnate, upper surface; 178A in color, lower surface; 181A in color.

*Leaf margins*.—Irregular crenate-serrate, undulate.

*Leaf attachment*.—Petiolate.

*Leaf arrangement*.—Alternate.

*Leaf orientation*.—Held upright and slightly pendulant.

*Leaf surface*.—Both surfaces glabrous, upper surface; moderately glossy, lower surface; matte.

*Leaf color*.—Young leaves upper surface; 143B and tinged with 200B to 200C, young leaves lower surface; between 143C and 146B and tinged with 183A at margins, mature leaves upper surface; color between N186C and 200A, closest to 200A, slightly to moderately tinged 148A, mature leaves lower surface; between 146B and 146C, moderately to strongly tinged 183A.

*Leaf size*.—Average of 19.5 cm in length, and 11.8 cm in width.

*Leaf quantity*.—About 45 leaves per lateral branch.

*Petioles*.—Average of 8.8 cm in length, 4 mm in width, upper surface; between 183A and 187B, lower surface; 185A in color, glabrous surface.

Flower description:

*Inflorescence type*.—Flowers are solitary in leaf axils.

*Lastingness of flowers*.—Average of 4 days, self cleaning.

*Flower size*.—An average of 13.6 cm in depth and 6.4 cm in diameter, up to 25 cm in spread when grown in a larger container or in the landscape.

*Flower fragrance*.—None.

*Flower shape*.—Rotate, typical *Hibiscus* shape.

*Flower number*.—Average of 2 per lateral stem.

*Flower aspect*.—Outward to slightly upright.

*Flower bud*.—Ovate in shape, an average of 4 cm in length and 2.6 cm in width, color; between 144B, tinged 183A to 183B, glabrous surface.

*Flower attachment*.—Petiolate.

*Petal number*.—5.

*Petal shape*.—Reniform to orbicular.

*Petal color*.—Upper surface when opening; between 69D and NN155D, flushed and veined 61B, base N45A, lower surface when opening; between 69D and NN155D, base 69B, veined NN155A, upper surface when fully open; between 69D and NN155D, flushed and veined 61B, base N45A, lower surface when fully open; between 69D and NN155D, base 69B, veined NN155A, fading to 75D, flushed with 68B, veined 61B to 61C, base 53A.

*Petal surface*.—Both surfaces glabrous, upper side glossy, lower side matte.

*Petal margins*.—Entire, overlapping.

*Petal apex*.—Obtuse.

*Petal size*.—Average of 7.6 cm in length and 8.3 cm in width.

*Sepal number*.—5.

*Sepal shape*.—Ovate.

*Sepal margin*.—Entire.

*Sepal size*.—Average of 4.3 cm in length and 2.3 cm in width (measured at the base of the free part).

*Sepal aspect*.—Rotate, lower 18.5% fused.

*Sepal surface*.—Both surfaces glabrous and matte.

*Sepal apex*.—Acute.

*Sepal base*.—Broadly cuneate and fused.

*Sepal color*.—Young upper surface; 145B, young lower surface; 144B, tinged 183A to 183B, mature upper surface; 145B, mature lower surface; 144B, tinged 183B to 183C.

*Calyx*.—Rotate in shape, average of 3 cm in length and 6.7 cm in diameter.

*Pedicels*.—None.

*Peduncles*.—Average of 6.5 cm in length, 3 mm in diameter, glabrous surface, held at an average angle of 40° (0°=straight on top of lateral branch), moderately strong, color; upper side 180A, lower side 146D with distal end 143C.

*Epicalyx*.—At the base of each flower is a ring of bracts, average of 13, linear in shape, curled upright, average of 2.1 cm in length and 2 mm in width, upper surface color 144C, lower surface color 144A to 144B, tip 176A.

Reproductive organs:

*Gynoecium.*—1 pistil, average of 4 cm in length, stigmas; club-shaped, an average of 5 and 158A in color, style; 3.8 cm in length and N155D in color, ovary; 145C in color and completely covered by the base of the style.

*Androecium.*—Stamens; average of 90, clustered and implanted in style, anthers; dorsifixed and orbicular in shape, 1 mm in length and 196B in color; filaments; 2 mm in length and 155A in color, pollen; moderate in quantity and 161A to 161B in color.

*Fruit/seeds.*—None observed to date.

It is claimed:

1. A new and distinct cultivar of *Hibiscus* plant named 'TAHI56' as herein illustrated and described.

* * * * *